United States Patent [19]

Michel et al.

[11] Patent Number: 5,504,122

[45] Date of Patent: Apr. 2, 1996

[54] RECOVERY OF DIMETHYL TEREPHTHALATE FROM POLYMER MIXTURES

[75] Inventors: Robert E. Michel; George M. Williamson, both of Wilmington, N.C.

[73] Assignee: E. I. Du Pont de Nemours and Company, Wilmington, Del.

[21] Appl. No.: 420,164

[22] Filed: Apr. 11, 1995

[51] Int. Cl.⁶ .................................................. C08J 11/04
[52] U.S. Cl. ..................... 521/48.5; 521/40.5; 521/41.5; 521/43; 521/43.5; 521/46.5; 525/445; 528/481; 528/486; 528/487; 528/489; 528/496; 528/503
[58] Field of Search .................................. 521/40.5, 41.5, 521/43, 43.5, 46.5, 48.5; 525/445; 528/481, 486, 487, 489, 496, 503

[56] References Cited

U.S. PATENT DOCUMENTS

| | | | |
|---|---|---|---|
| 5,120,768 | 6/1992 | Sisson | 521/46.5 |
| 5,393,916 | 2/1995 | Gamble | 560/78 |
| 5,395,858 | 3/1995 | Schwartz, Jr. | 521/48 |

*Primary Examiner*—Samuel A. Acquah

[57] ABSTRACT

Dimethyl terephthalate is recovered from polymer mixtures containing polymers of terephthalic acid and glycol and a chloride polymer, by adding base to neutralize the hydrochloric acid formed by the degradation of the chloride polymer.

7 Claims, No Drawings

RECOVERY OF DIMETHYL TEREPHTHALATE FROM POLYMER MIXTURES

FIELD OF THE INVENTION

This invention relates to the recovery of dimethyl terephthalate from mixtures of polymers containing (1) a polymer of terephthalic acid and a glycol and (2) a chloride containing polymer, by methanolysis.

BACKGROUND OF THE INVENTION

Published European Patent Application 0,484,963 A2 of R. E. Michel (Published May 13, 1992) discloses the preparation of dimethyl terephthalate by the methanolysis of polymers containing terephthalic acid units and glycol units. These polymers may be mixed with other materials such as polyvinylidene chloride—see the table runs 8 and 9.

U.S. Pat. No. 3,633,780 discloses burning polyvinyl chloride bottles in the presence of $CaCO_3$ which reacts with the hydrochloric acid liberated.

European Patent 254,538 discloses burning waste containing polyvinyl chloride and neutralizing the resulting gas by passing it through a dry alkaline material.

Japanese Patent 54,052,873 discloses spreading basic calcium compounds over polyvinyl chloride to neutralize hydrochloric acid formed during incineration.

Polyvinylidene chloride (PVDC) is often used to coat poly(ethylene glycol) terephthalate (PET) film in order to improve the adhesion of other coatings and to improve barrier properties. In addition another chloride containing polymer, polyvinyl chloride (PVC), is used for bottle manufacture and cannot be separated from poly(ethylene glycol) terephthalate (PET) using existing sink/float technology. These chloride polymers decompose at temperatures well below the melt temperature of poly(ethylene glycol) terephthalate (PET) to liberate HCl. The hydrochloric acid generated in the methanolysis reactor resulting from the decomposition of chloride containing polymers spreads chlorides throughout the purification system and results in general corrosion and/or stress cracking of stainless steel equipment.

SUMMARY OF THE INVENTION

The present invention is a process for the preparation of dimethyl terephthalate from a polymer mixture containing (1) a polymer of terephthalic acid and a glycol and (2) a chloride containing polymer, which comprises (a) combining said polymer mixture with a base whose hydrolysis constant is greater than that of the chloride ion (b) subjecting the product of step (a) to methanolysis and (c) recovering dimethyl terephthalate.

The amount of base added should be no more than approximately equal on a mole basis to the amount of chloride contained in the polymer mixture. Since only labile chloride need be reacted to achieve the benefits of the invention, the amount of base added is usually only one half to two thirds of the molar amount of chloride in the polymer. Usually the chloride containing polymer is selected from the group consisting of polyvinylidene chloride and polyvinyl chloride. Usually the base is selected from the group consisting of salts of carboxylic acids, salts of biphosphates, salts of bisulfites, alkali metal hydroxides, alkaline earth metal hydroxides. Usually the methanolysis is carried out by treating the product of step (a) in a reaction zone with methanol vapor at a temperature above 230 degrees C., and continuously removing vapors of methanol, dimethyl terephthalate and glycol from the reaction zone. Usually the vapors removed from the reaction zone contain about 3 moles of methanol for every mole of dimethyl terephthalate. A preferred base is sodium hydroxide.

By use of the invention the chlorides can be restricted to the dissolution-reactor system by base addition to the reactor feed tank.

DETAILED DESCRIPTION

A description of the over all methanolysis process can be found in European published application 0,484,963 A2. Base addition to the feed system for methanolysis can be accomplished by any number of means. A solid base could be added through the solid feed system with the poly(ethylene glycol) terephthalate (PET) while a liquid base could be added directly to the feed tank. The mode of addition should be one in which the base is well dispersed in the melter-dissolver. A base in this instance is any material whose hydrolysis constant is greater than that of the chloride ion. This would include materials such as salts of carboxylic acids, salts of biphosphates and bisulfites, as well as the alkali and alkaline earth hydroxides.

In order to minimize yield losses of dimethyl terephthalate, excess base, greater than one equivalent per "mole" of chloride containing polymer, should be not be used.

Most of the low priced poly(ethylene glycol) terephthalate (PET) scrap, which is economically suited for conversion back to its reactants, contains some chloride containing polymer. If the chlorides are not contained in the feed preparation and the reactor system, as relatively innocuous salts, the remainder of the plant will be subject to severe corrosion.

Good dispersion of the base is an important variable as regards the efficiency of the operation of this process. It is also important to control the amount of base so as to limit the formation of terephthalate salts which would reduce the yield of usable products form the methanolysis. However, if salts of terephthalic acid are used as the base in this process, their conversion to terephthalic acid by HCl formed from the decomposition of the chloride containing polymer will increase the yield of usable intermediates for this process.

EXAMPLE

Preliminary Test: Determine whether base would neutralize hydrochloric acid formed on heating a mixture containing poly(ethylene glycol) terephthalate and PVDC.

The apparatus consisted of a well insulated and electrically heated flask and vapor discharge tube leading to two scrubbers in series which contained std. NaOH. The flask was also equipped with an inlet for a nitrogen sweep and a mechanical stirrer. To start a run the flask was charged with a 60–40 mixture of poly(ethylene glycol) terephthalate (PET) and dimethyl terephthalate (DMT) and heated to >260 C. A 10 g pellet of dimethyl terephthalate (DMT) containing 1 g of PVDC was added to begin a run. A gentle nitrogen purge was started and heating continued for one hour. In some instances an equivalent amount of base, based on the theoretical amount of Cl available from the polyvinylidene chloride (PVDC), was well dispersed in the melt before addition of the polyvinylidene chloride (PVDC) containing pellet. The gas scrubbing efficiency was checked by vaporizing 48% HCl in the apparatus and by decomposing polyvinylidene chloride (PVDC) in the absence of poly(ethylene glycol) terephthalate (PET)/dimethyl terephthalate (DMT).

The value for HCl was determined by acid base titration of the scrubbers and the value for chloride was determined by potentiometric titration with silver nitrate. The effect of dispersion was checked by decreasing the stirring speed.

EFFECT OF CAUSTIC ON GASEOUS HCL

| Feed | g.PET/ DMT | Temp. | Base Add. | HCl(1) | Cl- |
|---|---|---|---|---|---|
| 5 ml 0.5N HCl | 0 | 240 | No | 100 | — |
| 1.00 g PVDC | 0 | 270 | No | 54 | 50 |
| 1.00 g PVDC | 200 | 265 | No | 30 | 28 |
| 1.00 g PVDC | 220 | 270 | Yes(2) | <1 | <1 |
| 1.00 g PVDC | 220 | 270 | Yes(3) | <1 | <1 |
| 1.00 g PVDC | 220 | 270 | Yes(4) | 14 | 13 |

(1)% volatile Cl, for tests using PVDC this number is theoretical and based on 2Cl/mole PVDC.
(2)One equivalent based on 2Cl/mole PVDC, NaOH.
(3)One equivalent based on 2Cl/mole PVDC, Na2TPA.
(4)Repeat of (2) with poor base dispersion.

The decomposition of PVDC in the absence of DMT it appears that only one chloride per "mole" of polymer is thermally liable. This is somewhat shown by the decomposition in PET/DMT. In any case, the results show that the addition of base, which has been well dispersed in the melt, eliminates the evolution of HCl vapor.

Example 1

Into a 2 L glass resin kettle bottom, equipped with a heating mantle, were placed 400 g of PVDC (1% by wt.) coated polyethylene terephthalate film. Heating was started. As the film began to melt 25% by weight, aqueous sodium hydroxide was sprayed in the kettle until the film was completely melted and a total of 6.6 g the caustic solution was used. The melted film was cooled, crushed, and placed in the methanolysis reactor.

Methanolysis of the above sample was conducted at 290 C. and 70 psig in the reactor described in EP 0,484,963 A2 (Published May 13, 1992). Liquid methanol flow to the reactor was 200 ml/hr. and the reaction was carried out for four hours.

Analysis of the condensed reactor effluent showed an 83% conversion to DMT, 88% conversion to ethylene glycol, and a 10% conversion to the mixed glycol-methyl ester of TPA. Five percent of the initial feed remained in the reactor as a cake below the methanol vapor feed line.

What is claimed is:

1. A process for the preparation of dimethyl terephthalate from a polymer mixtures containing (1) a polymer of terephthalic acid and a glycol and (2) a chloride containing polymer, which comprises (a) combining said polymer mixture with a base whose hydrolysis constant is greater than that of the chloride ion (b) subjecting the product of step (a) to methanolysis and (c) recovering dimethyl terephthalate.

2. The process of claim 1 in which the amount of base is no more than approximately equal on a mole basis to the amount of chloride contained in the polymer mixture.

3. The process of claim 2 in which the chloride containing polymer is selected from the group consisting of polyvinylidene chloride and polyvinyl chloride.

4. The process of claim 3 in which the base is selected from the group consisting of salts of carboxylic acids, salts of biphosphates, salts of bisulfites, alkali metal hydroxides, alkaline earth metal hydroxides.

5. The process of claim 4 in which the methanolysis is carried out by treating the product of step (a) in a reaction zone with methanol vapor at a temperature above 230 degrees C., and continuously removing vapors of methanol, dimethyl terephthalate and glycol from the reaction zone.

6. The process of claim 5 in which the vapors removed from the reaction zone contain about 3 moles of methanol for every mole of dimethyl terephthalate.

7. The process of claim 6 in which the base is sodium hydroxide.

* * * * *